United States Patent
Vancamberg et al.

(10) Patent No.: US 12,414,750 B2
(45) Date of Patent: *Sep. 16, 2025

(54) SYSTEM AND METHOD FOR TRAINING SENSOR-GUIDED X-RAY MAMMOGRAPHY SYSTEM

(71) Applicant: GE Precision Healthcare LLC, Waukesha, WI (US)

(72) Inventors: Laurence Vancamberg, Poissy (FR); Serge Muller, Guyancourt (FR); Zhijin Li, Paris (FR)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/767,805

(22) Filed: Jul. 9, 2024

(65) Prior Publication Data
US 2024/0358337 A1    Oct. 31, 2024

Related U.S. Application Data

(63) Continuation of application No. 17/712,555, filed on Apr. 4, 2022, now Pat. No. 12,064,277.

(51) Int. Cl.
*A61B 6/50* (2024.01)
*A61B 6/00* (2024.01)
*A61B 6/04* (2006.01)
*G06N 3/08* (2023.01)

(52) U.S. Cl.
CPC ............ *A61B 6/502* (2013.01); *A61B 6/0435* (2013.01); *A61B 6/547* (2013.01); *G06N 3/08* (2013.01)

(58) Field of Classification Search
CPC ....... A61B 6/502; A61B 6/0435; A61B 6/547; A61B 10/0233; A61B 2034/2065;
(Continued)

(56) References Cited

U.S. PATENT DOCUMENTS 12,064,277 B2 *   8/2024   Vancamberg ............ A61B 6/12
2021/0307711 A1   10/2021  Vancamberg

OTHER PUBLICATIONS

Amelia Jimenez-Sanchez et al.; "Memory-aware curriculum federated learning for breast cancer classification"; arXiv:2107.02504v1 [cs.CV] Jul. 6, 2021—(12) pages.
(Continued)

*Primary Examiner* — Courtney D Thomas

(57) ABSTRACT

Various methods and systems are provided for breast positioning assistance during mammography and image guided interventional procedures. In one example, a sensor detection system is utilized to evaluate one or more of a patient position, a breast position, and breast anatomy to determine if the patient and breast are adjusted to desired positions preferred for a desired view and imaging procedure prior to acquiring x-ray images, with real-time feedback provided to guide the user to position the breast and/or the patient based on the evaluation. The evaluation is performed by an artificial intelligence (AI) model stored on the x-ray mammography system that is trained using sensor data obtained from imaging procedures performed using the x-ray mammography system and fashioned into training datasets by a training module located on the x-ray mammography system.

20 Claims, 4 Drawing Sheets

(58) Field of Classification Search
CPC ....... A61B 2090/376; A61B 6/04; A61B 6/12; A61B 6/0414; A61B 6/42; A61B 6/5211; G06N 3/08; G06N 3/098; G06N 3/0464; G16H 40/67
See application file for complete search history.

(56) References Cited

OTHER PUBLICATIONS

Dong et al.; "Federated Contrastive Learning for Decentralized Unlabeled Medical Images"; Department of Computer Science, University of Oxford, Oxford, UK; nanqing.dong@cs.ox.ac.uk—(10) pages, (2021).

Pan et al.; "Collaborative Image Synthesis and Disease Diagnosis for Classification of Neurodegenerative Disorders with Incomplete Multi-modal Neuroimages"; School of Computer Science and Engineering, Northwestern Polytechnical University, Xi'an 710072, Shaanxi, China; yspan@mail.nwpu.edu.cn—(8) pages, (2021).

Roth et al.; "Federated Learning for Breast Density Classification: A Real-World Implementation"; arXiv:2009.01871 v3 [eess.IV] Oct. 20, 2020—(11) pages.

Shan et al.; "A Coherent Cooperative Learning Framework Based on Transfer Learning for Unsupervised Cross-domain Classification"; Shanghai Key Laboratory of Multidimensional Information Processing, School of Communication and Electronic Engineering, East China Normal University, Shanghai, China; ywen@cs.ecnu.edu.cn—(11) pages, (2021).

\* cited by examiner

SYSTEM AND METHOD FOR TRAINING SENSOR-GUIDED X-RAY MAMMOGRAPHY SYSTEM

CROSS-REFERENCE TO RELATED APPLICATIONS

The present application is a continuation of U.S. patent application Ser. No. 17/712,555, filed on Apr. 4, 2022, the entire contents of which is hereby incorporated by reference.

FIELD OF THE DISCLOSURE

Various methods and systems are provided for breast positioning assistance during mammography and image guided interventional procedures. In one example, a vision system is utilized with an x-ray imaging system to evaluate one or more of a patient position, a breast position, and breast anatomy to determine if the patient and/or breast need to be adjusted to desired positions preferred for a desired view and imaging procedure. Further, the evaluation can be conducted via an on-site trained artificial intelligence employed within the imaging system to provide real-time feedback to guide the user to position the breast and/or the patient.

BACKGROUND OF THE DISCLOSURE

Embodiments of the invention relate generally to x-ray medical imaging, and more particularly to systems and methods to perform mammography exams, or digital breast tomosynthesis (DBT).

X-ray mammography (MG) is an x-ray imaging modality used to scan breasts for screening, diagnosis and/or interventional examinations. The effectiveness of x-ray mammography is affected by numerous factors, one of which is the two-dimensional (2D) rendering of images obtained.

Alternative systems to 2D x-ray mammography are also known for breast imaging. For example, a digital breast tomosynthesis (DBT) system is a dedicated mammography system that acquires several (e.g., tens of) angularly offset projection x-ray images and uses the resulting x-ray image data to reconstruct three-dimensional (3D) image datasets.

The 2D and/or 3D images obtain in a mammography imaging procedure can detect one or more cancers of a breast. Accurate interpretation of a mammography image (also known as mammogram) and detection of a breast cancer relies on generation of high quality mammograms. A key factor affecting the quality of a mammogram is breast positioning. Failure to position the breast properly may result in mammographic artifacts and tissue exclusion, and consequently, missed cancers. The level of training and experience of the technologists can significantly affect image quality. For example, technologists with less/intermediate training and/or experience may not position the breast properly, and as result, recall rates and missed cancers may be higher.

Further, previous approaches for the evaluation of the positioning of a breast in mammography images involve the technologist reviewing the x-ray image that has already been acquired. Consequently, a radiation dose has already been delivered to the patient even though the breast was not well positioned for the image, with a subsequent dose being required to obtain a proper mammography image after the breast is positioned properly. This duplication of the radiation dose delivered to the patient is highly undesirable. In addition, even during the review of the x-ray images, some technologists may not evaluate the x-ray image correctly, which also increases recall rates and reduces confidence in any diagnosis resulting from the mammography images.

To assist in the detection of a breast positioning error prior to obtaining an x-ray image of the incorrectly positioned breast, mammography imaging systems have been developed that include one or more cameras, such as that disclosed in US Patent Application Publication No. US2021/0307711, entitled Methods And Systems For User And/Or Patient Experience Improvement In Mammography, the entirety of which is expressly incorporated herein by reference for all purposes. The cameras obtain real-time images of the position of the breast and the imaging system for comparison with a user input for the desired position for the breast and the associated mammography image to be obtained. If the camera images indicate a position for the breast that does not correspond to the desired position of the user input, the imaging system can alert the operator to the improper breast position, such that the operator can make the necessary correction prior to delivering an unnecessary radiation does to the patient.

However, one drawback with regard to this mammography imaging system involves the training required for the imaging system to properly compare the camera images with the user input in order to provide an accurate assessment of the actual breast position relative to the desired and/or selected position based on the user input. In prior art imaging systems, the training of the artificial intelligence contained within the imaging system and utilized for performing the comparison requires a training set including a large amounts of data containing mammography images and associated camera images in order to enable the artificial intelligence to learn the proper associations between the mammography images and the camera images to output proper comparison results. As there are significant concerns and regulations regarding the collection and use of patient data in order to provide the required training dataset for the artificial intelligence, the process of obtaining a sufficient training dataset as well as the requirements regarding the protection of, e.g., rendering anonymous, the data forming the training dataset while in use during the training of the artificial intelligence has significant time and expense limitations.

As a result, it is desirable to develop a system and method for performing the training of an artificial intelligence for a mammography imaging system that can utilize image data continuously obtained from an on-site imaging system, but without removing the data from the clinical environment or altering the operation or workflow for the utilization of the imaging system within the clinical environment.

SUMMARY OF THE DISCLOSURE

According to one aspect of an exemplary embodiment of the disclosure, an x-ray mammography system includes a gantry disposed on a support surface and including an x-ray source, an x-ray detector alignable with the x-ray source, an image processing system operably connected to the gantry to control operation of the x-ray source and x-ray detector to generate x-ray image data in an imaging mode for the mammography system, the image processing system including a processor for processing the x-ray image data from the detector, a database operably connected to the processor and storing instructions for operation of a feature detection AI model and a training module therein, and a sensor detection system disposed on the gantry and operably connected to the image processing system, the sensor detection system including at least one sensor operable to generate sensor data of the gantry or a patient. The training module is configured to receive at least one of user input parameters for an imaging procedure to be performed by the x-ray mammography system, one or more internal system outputs from control algorithms stored in the database, and combinations thereof, and sensor data from the sensor detection system to form a training dataset for use in training the feature detection AI model.

According to still another aspect of an exemplary embodiment of the present disclosure, a method for training a sensor-based feature detection artificial intelligence (AI) model for an x-ray mammography system. The method includes providing an x-ray mammography system including a database for storing instructions for operation of a feature detection AI model, and a sensor detection system including a sensor for generating sensor data of the x-ray mammography system or a patient. The method also includes inputting parameters for an imaging procedure to be performed by the x-ray mammography system. The method also includes positioning a patient breast proximate the x-ray mammography system. The method also includes obtaining sensor data with the sensor detection system. The method also includes providing at least one of the input parameters, one or more internal system outputs from control algorithms stored in the database, and combinations thereof, with the sensor data to a training module to form a training dataset. The method also includes providing the training dataset to the feature detection AI model.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
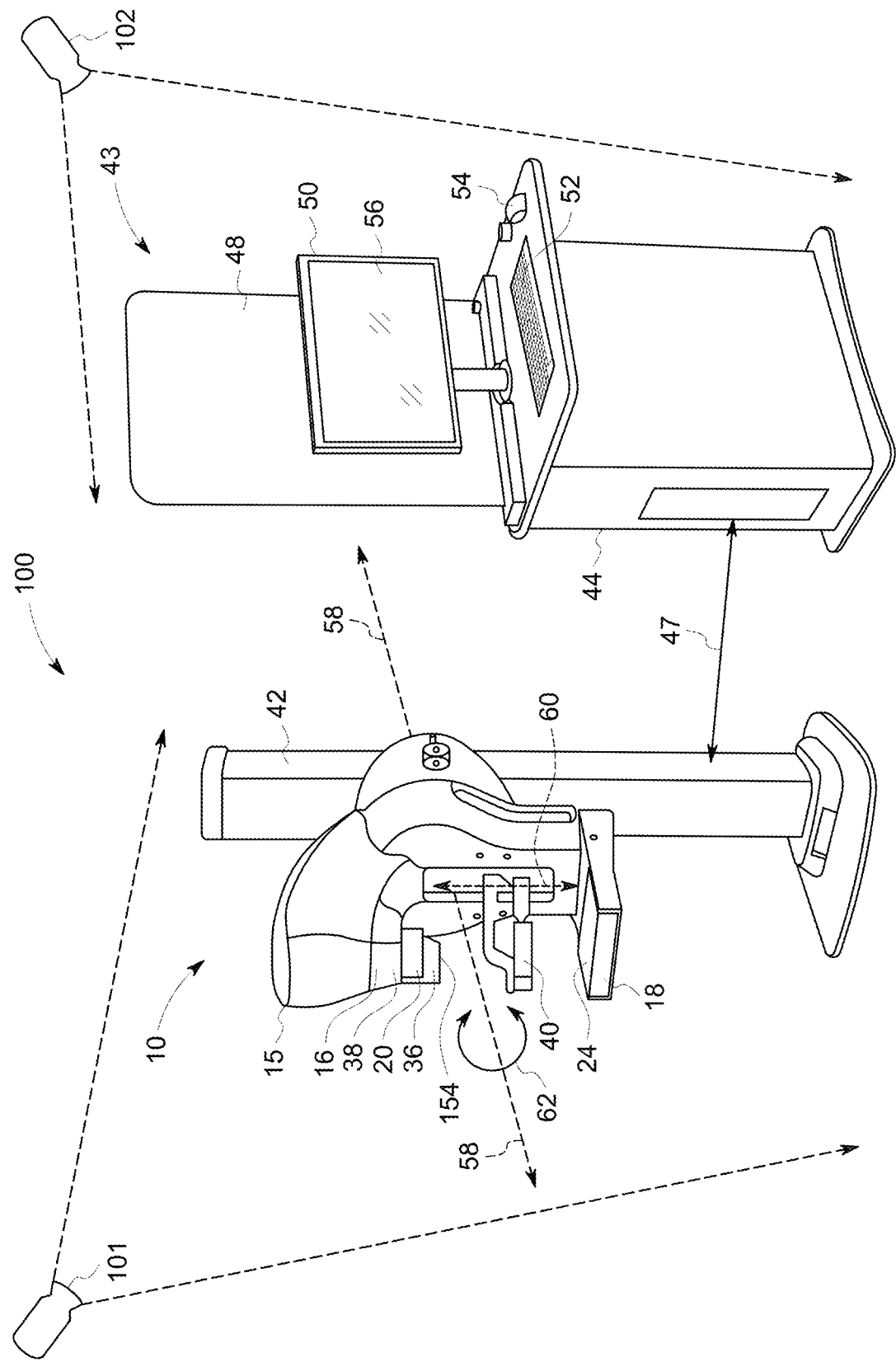
FIG. 1 is a schematic illustration of a mammography system including a vision sensing system, according to an embodiment of the disclosure.
Figure 2:
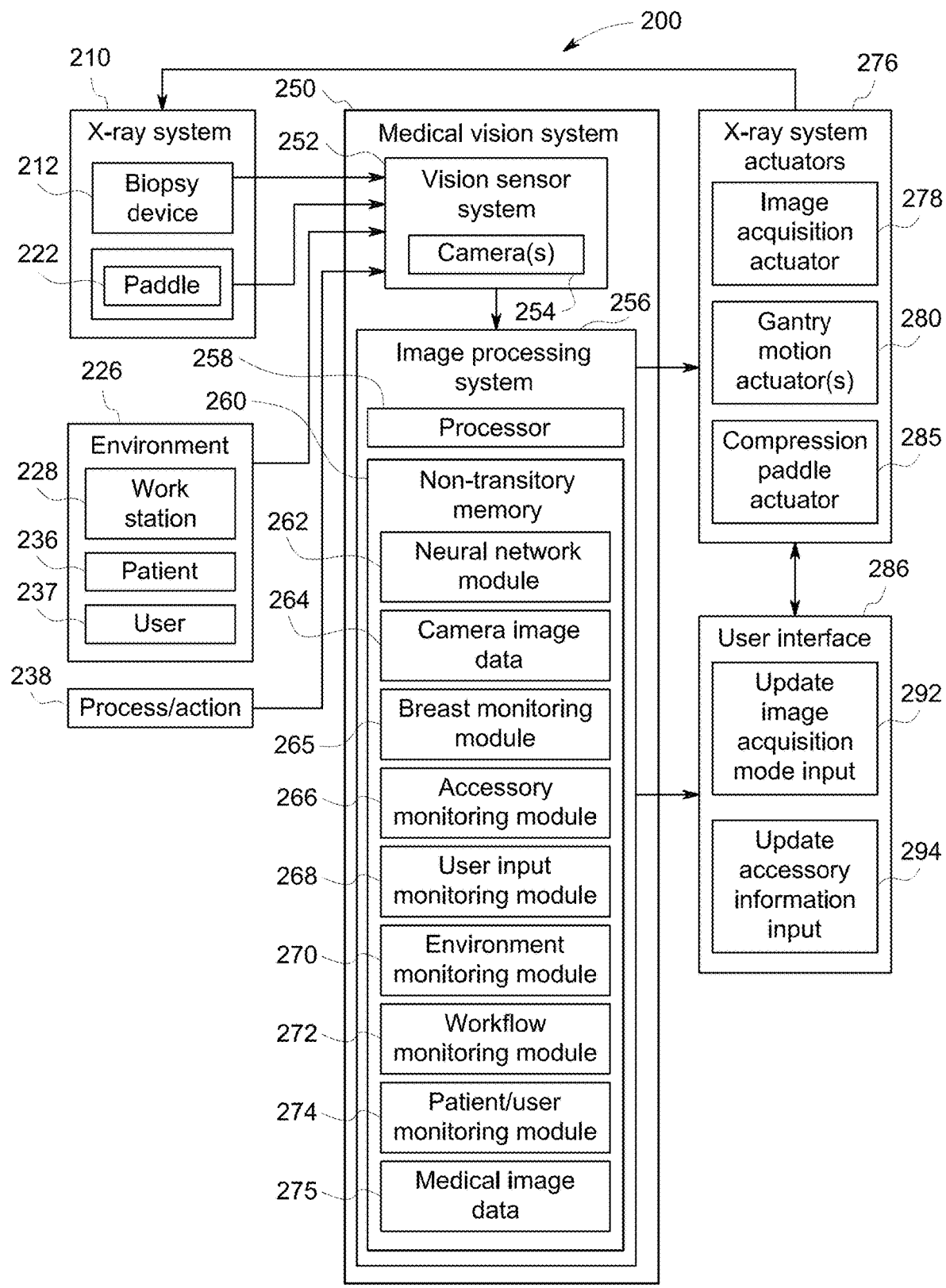
FIG. 2 is block diagram of a mammography system including a medical vision system, illustrating a plurality of objects sensed by the medical vision system and a plurality of actuators controlled based on the objects sensed, according to an embodiment of the disclosure.

The following description relates to various embodiments for an x-ray system for mammography and biopsy procedures. An exemplary embodiment of an x-ray imaging system is shown at FIG. 1, which includes a sensor system, including one or more sensors, e.g., a time-of-flight sensor, a lidar sensor, or a vision sensors, such as cameras, to detect the positions of one or more of an accessory associated with each procedure, the body part involved in the procedure, one or more objects in the environment surrounding the system, a patient, and a user. Based on the position detection by the sensor system, the x-ray imaging system including the sensor system may evaluate one or more of a breast morphology, a breast position, a patient morphology, a patient position, a user morphology, and a user position. A block diagram of one or more objects and actions detected by the sensor system, including the sensor, such as a camera, and one or more actuators of the x-ray system adjusted based on the one or more objects and actions detected is illustrated at FIG. 2. A controller of the x-ray mammography system may be configured to operate a training module to train an artificial intelligence (AI)/neural network model to evaluate one or more of a breast position and breast morphology, a patient position and patient morphology, a user position and user morphology, and a mammography system configuration, including accessories positioned thereon, such as biopsy procedure accessories, using sensor and/or position data from the sensor system within the clinical environment for the imaging system, as illustrated with the exemplary system and method of the high-level flow chart at FIG. 3. Furthermore, another exemplary system and method for the training of the AI/neural network model employed by the controller for making the breast position and/or patient position evaluation, and for providing real-time feedback for breast position adjustment during use of the x-ray imaging system is illustrated and described with regard to FIG. 4.

During an x-ray imaging procedure, such as mammography or DBT imaging procedure, and during an x-ray image-guided interventional procedure, such as DBT-guided biopsy, CESM biopsy, stereotactic biopsy, etc., positioning the breast plays an important part in obtaining high quality images that demonstrate the various areas of the breast. Further, depending on the view, some of the landmarks for positioning may differ. Typically, the determination of whether the breast is positioned to provide high quality mammograms cannot be made until the mammogram is in the process of being obtained. The inventors herein have identified the above-mentioned issues and provide methods and systems for improving positioning of breast prior to initiating acquisition. In particular, methods and systems are provided for evaluating breast position and patient body position prior to imaging and providing real-time feedback for improving breast and patient positioning. In one embodiment, a first detection sensor, used for evaluating the patient body position, captures position data, e.g., an image of the patient and the x-ray system, and a second detection sensor, used for evaluating breast position, captures compressed breast position data and/or image(s). The sensor position data, e.g., camera images, obtained from the first and the second detection sensors is then input into an artificial intelligence (AI)/neural network based position data/image processing model, which evaluates the input position data and/or images for a desired breast positioning framework (that is, for inclusion of breast anatomical landmarks based on the view), and further evaluates patient position, and provides real-time feedback to the technologist/user for one or more of patient and breast position correction, through the user interface. Details of evaluating one or more of patient position and breast position for improving breast position for imaging with the mammography system are further described below.

In addition to the evaluation provided by the AI/neural network based image processing model, the AI based image processing model or AI is trained or built to perform the evaluations described previously utilizing data obtained during the normal operation of the x-ray imaging system in a clinical setting or environment. More specifically, the x-ray imaging system receives user inputs, such as user console inputs regarding, e.g., laterality, view and/or patient position, and system outputs, such as the breast position monitoring result, that are employed by the x-ray imaging system in order to obtain the sensor position data and/or images, and mammography images for a particular imaging procedure performed by the x-ray imaging system. These inputs and/or outputs for each imaging procedure can be provided in various combinations with the sensor position data and/or images as training data to a training system or training manager operably connected to the x-ray imaging system in order to train the AI/neural network using the actual inputs to and outputs from the x-ray imaging system for the imaging procedure. Using the data including these inputs and/or outputs from imaging procedures performed by the x-ray imaging system, the training manager can operate to train the AI in a continuous manner during regular operation of the x-ray imaging system without removing any of the data obtained in the imaging procedures from the imaging system and without altering the normal workflow of operation of the x-ray imaging system.

Referring to FIG. 1, a mammography system 100 including an x-ray system 10 for performing a mammography procedure is shown, according to an exemplary embodiment. The x-ray system 10 may be a tomosynthesis system, such as a digital breast tomosynthesis ("DBT") system, such as that shown and disclose in US Patent Application Publication No. US2021/0703311, entitled Methods And Systems For User And/Or Patient Experience Improvement In Mammography, the entirety of which is expressly incorporated herein by reference for all purposes. The x-ray system 10 may be used to perform one or more procedures including digital tomosynthesis imaging, and DBT guided breast biopsy. Further, the x-ray system 10 may be utilized to perform a mammography imaging procedure, wherein one or more views including a craniocaudal (CC view) and a mediolateral oblique (MLO view) of a breast are obtained. The x-ray system may be further used to perform other x-ray screening and diagnostic imaging procedures, including CESM, and contrast enhanced DBT (CE-DBT) diagnostic imaging, and interventional procedures, including CESM-guided biopsy and stereotactic procedures.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about a vertical axis perpendicular to a horizontal detection surface of the detector 18.

The radiation source 16 is directed toward a volume or object to be imaged, and is configured to emit radiation rays at desired times and to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of an object imaged.

In some exemplary embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure 42 along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, the radiation detector 18, the compression paddle 40, and a biopsy device. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 56, a keyboard 52, mouse 54, and/or other appropriate user input devices that facilitate control of the system 10 via a user interface 50.

Further, the x-ray system 10 may include a second control station (not shown) including a second user interface with a second display portion having appropriate input features to facilitate control of the system 10 and view one or more images captured by one or more of the vision system and x-ray system 10. The second control station may be positioned near the x-ray system and may be coupled (wired or wirelessly) to the x-ray system 10. Specifically, the second control station may be positioned such that the user, while adjusting breast and/or patient position, can look at the second display portion and/or the second user interface. Thus, the positioning of the second control station may allow the user to simultaneously view the real-time sensor/camera feedback and adjust patient and/or breast position.

Through its processors and controllers, the controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part. The controller 44 may also control how information, including images 42 and data acquired during the operation, is processed, displayed, stored, and manipulated. The different processing steps, including receiving one or more signals from one or more sensors, receiving user input, evaluating the received signals/input, image processing, determining reconstruction error, outputting operation parameters including error indications, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays emitted by the radiation source 16. In particular, during imaging with the x-ray system, a projection image of the imaging body part may be obtained at the detector 18. In some exemplary embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44 and displayed via the display portion 50 on the interface 56.

During mammography, the gantry 15 may be adjusted at different angles to obtain images at different orientations, such as a craniocaudal (CC) image and a mediolateral oblique (MLO) view. Further, during obtaining mammography views (e.g., CC and MLO views) the gantry 15, the compression paddle 40, and the detector 18 may be rotated along line 62 as a single unit about the axis 58. In other examples, the gantry 15 may be rotated about the axis 58 while the compression paddle 40 and the detector 18 remain stationary.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. During tomosynthesis, similar to mammography, the breast is compressed between the compression paddle 40 and the detector 18. The radiation source 16 is then rotated from $-\theta$ to $+\theta$, and a plurality of projection images of the compressed breast is obtained at regular angular intervals over the angular range. For example, if the angular range of the x-ray system is +/−11 degrees, twenty-two (22) projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional DBT image of the breast.

Furthermore, the x-ray system 10 may be configured to perform a DBT-guided biopsy procedure. Accordingly, in some exemplary embodiments, the system 10 may further include a biopsy device (not shown) comprising a biopsy needle for extracting a tissue sample for further analysis in any suitable manner.

The mammography system 100 may further include one or more position/detection sensors for sensing and/or obtaining position data for one or more components and accessories of the mammography system 100. The one or more detection sensors may include a first sensor 101 and a workstation sensor 102, as shown in FIG. 1. The first sensor 101 and the second sensor 102 can each be formed as a vision sensor, e.g., a camera including a camera for obtaining RGB images, a depth sensor, e.g., a time-of-flight sensor, a combination thereof, a force/pressure sensor and/or a speed sensor, e.g., employed where the system 100 is learning/being trained for an optimal compression profile from motion analysis from the position data/image(s), and may be configured to sense one or more components and accessories associated with the x-ray system 10. Further, the first sensor 101 may be configured to sense one or more of a user and patient morphology and actions while the workstation sensor 102 may be utilized to monitor user position and/or action at the workstation. While the present example, illustrates the first sensor 101 and the second sensor 102 being formed as two cameras for implementing vision sensing for the mammography system 100, it will be appreciated that the sensor system may include additional sensors, e.g., cameras, or fewer sensors, e.g., cameras, as discussed further below. Further, the one or more sensors may include a second sensor 154 coupled to the x-ray system 10. The second sensor 154 can be formed similarly to the first sensor 101, such as a camera, and may be utilized for capturing position data and/or camera images of the compressed breast in the imaging volume. As such, position data and/or camera images obtained with the second sensor 154 may be utilized for evaluating breast position prior to acquiring x-ray projection images.

The second sensor 154 may be coupled to the gantry 15 such that a field of view of the second sensor 154 is in alignment with respect to the field of view of the x-ray system 10, particularly with respect to the radiation source 16 located within the gantry 15. The second sensor 154 may be used to monitor breast position and breast anatomical landmarks of the patient during a procedure, such as mammography imaging, DBT imaging, or image-guided biopsy, performed by the x-ray system 10. In one example, the second sensor 154, as well as other sensors 101, 102, etc., may be configured as an RGB-D camera that combine depth information with RGB color information. Further, the second sensor 154 may be communicatively coupled to a controller 44 of the x-ray system 10, and one or more position data/sensor images and/or sensor image sequences captured by the second sensor 154 may be stored in a non-transitory memory of the controller 44. Further, the second sensor 154 may be configured to capture movements and/or action. For example, a sequence of sensor images over a duration may be obtained, which may be used for action recognition.

It will be appreciated that in some embodiments the second sensor 154 may be positioned such that the imaging volume including the compression paddle 40, the detector 18, and the compressed breast is positionally located and/or visualized via the second sensor 154. In some embodiments, the second sensor 154 may be positioned so as to monitor and evaluate a partial portion of the patient in addition to compressed breast position. That is, the second sensor 154 may also be used to capture partial portions of the patient (e.g., patient shoulder) and thus, provide a partial view of the patient in addition to views of compressed breast.

Taken together, the second sensor 154 may be adjusted (e.g., by adjusting a position of the second sensor 154) to view and/or capture one or more of the imaging volume (including the compression paddle, the detector, and the compressed breast), the imaging volume and a margin volume, and the imaging volume and a partial portion of the patient.

Further, in one example, the position data and/or sensor images captured by the second sensor 154 may be preprocessed to extract relevant image data, and the processed image data may be used as input into an artificial intelligence based deep learning model (stored in a controller, an edge device connected to the controller, a cloud in communication with the controller, or any appropriate combination thereof) comprising a neural network such as a convoluted neural network for evaluating breast position based on breast anatomical landmarks detected during positioning of the breast for various imaging and image-guided procedures with the x-ray system 10. Some of the breast anatomical landmarks (also referred to as breast structures) may vary depending on the view (e.g., CC or MLO view) and procedure (e.g., mammography or DBT), while there may be some common breast anatomical landmarks or breast structures that are evaluated for breast positioning at each view.

Returning to FIG. 1, the one or more vision sensors may be communicatively coupled to the controller 44. Details of the various components of the mammography system 100 that may be sensed and monitored by the first sensor 101, second sensor 154 and/or workstation sensor 102, and the various actuators of the mammography system 100 that may be adjusted in response to the sensing and monitoring by the sensors will be further elaborated with respect to FIG. 2 below.

Turning to FIG. 2, a block diagram of a mammography system 200 is shown. The mammography system 200 may be a non-limiting example of the mammography system 100 at FIG. 1. Briefly, the mammography system 200 may be utilized to perform one or more of a mammography procedure, such as a routine mammogram, a digital breast tomosynthesis, and a biopsy procedure, such as a stereotactic biopsy or DBT-guided biopsy. The mammography system 200 may include a medical vision system 250 having at least a sensor system 252 and a processing system 256 to perform one or more of sensing, monitoring, and analyzing of one or more accessories and components associated with the mammography system 200. Further, the mammography system 200 may be automatically adjusted, controlled, and set-up via the processing system 256 based on the input from the sensor system 252 and the analysis of the input by the processing system 256, to improve workflow, breast positioning, and patient positioning, during one or more of the mammography and biopsy procedures performed with the mammography system 200. The processing system 256 may be a non-limiting example of controller 44 at FIG. 1, and may be configured to receive signals form one or more sensor systems of the mammography system 200, including the sensor system 252, as further discussed below. The processor may be further configured to analyze the data received from the sensor systems and adjust operation of the mammography system 200 via one or more x-ray system actuators 276, in addition to providing real-time feedback including one or more alerts and indications to one or more of the user and the patient via a user interface 286 of the mammography system 200 as further discussed below.

The mammography system 200 may include an x-ray system 210, and a medical vision system 250. X-ray system 210 may be an example of x-ray system 10 discussed at FIG. 1. In one exemplary embodiment, the x-ray system 210 may be configured as a medical imaging modality for performing a mammography procedure to image and analyze a body part of a patient, such as a breast. In another exemplary embodiment, the x-ray system 210 may be configured for performing a biopsy procedure, such as an x-ray guided biopsy to obtain a tissue sample from the body part of the patient. Further, the x-ray system 210 may be converted from a mammography system for obtaining medical scan images to a biopsy system to perform a biopsy procedure for extracting tissue for evaluation. When the x-ray system 210 is utilized to perform a biopsy procedure, a biopsy device 212 may be coupled to the x-ray system 210. The biopsy device 212 may be an example of the biopsy device described at FIG. 1, and may include a compression paddle 222 for supporting the body part and holding the body part so as to reduce movement during biopsy. The compression paddle 222 is an example of compression paddle 40 described with respect to FIG. 1, and the mammography system may be configured to monitor, via the medical vision system 250, one or more of components, such as the biopsy device 212, different components of the biopsy device 212, and accessories, such as the compression paddle 222. As an example, during a mammography exam or a biopsy exam, in order to adjust breast position, the user may move the compression paddle. The vision system 250 may detect a movement of the compression paddle 222, and after compression, based on the changed position of the compression paddle, the controller may command adjustment of a collimator such that the breast is within the field of view of the x-ray system.

Furthermore, in some embodiments, the vision system 250 may be utilized to determine a final (locked) position of the compression paddle 222. The final compression paddle position may indicate that the breast is in position for imaging. In one example, upon confirming the final position of the compression paddle, a breast position of the compressed breast may be evaluated, and as such, a breast position evaluation interface may be launched and breast position evaluation may be performed with the vision system 250. Upon confirming, with the vision system 250, that the compressed breast is in a desired position for imaging, the mammography system may be used to begin x-ray image acquisition of the compressed breast. In another example, upon confirming the final position of the compression paddle, one or more of a breast position and a patient position may be evaluated with the vision system 250. Upon confirming that one or more of the breast position, the patient position, and the user position are at respective desired positions for imaging, the mammography system may be used to begin x-ray image acquisition.

The mammography system 200 may be further configured to monitor an environment 226 surrounding the x-ray system 210 using the medical vision system 250.

As indicated above, the medical vision system 250 includes a sensor detection system 252 comprising one or more position detecting sensors, e.g., cameras 254, and an image processing system 256 comprising a processor 258, and a non-transitory memory 260. The sensor system 252 may be communicatively coupled to the image processing system 256. Specifically, the processing system 256 may receive one or more signals from the one or more cameras 254 of the system 252. The one or more sensors or cameras 254 of the system 252 may be similar to sensors or cameras 101, 102 and 154 discussed with respect FIG. 1, and as such, the one or more sensors/cameras 254 may sense the mammography system 200 and its components, accessories, and environment. Data from the one or more sensors/cameras 254 may be sent to the processing system 256 for further analysis and storage.

The processing system 256 includes a processor 258 configured to execute machine readable instructions stored in the non-transitory memory 260. Processor 258 may be single core or multi-core, and the programs executed thereon may be configured for parallel or distributed processing. In some embodiments, the processor 258 may optionally include individual components that are distributed throughout two or more devices, which may be remotely located and/or configured for coordinated processing. In some embodiments, one or more aspects of the processor 258 may be virtualized and executed by remotely-accessible networked computing devices configured in a cloud computing configuration. According to other embodiments, the processor 258 may include other electronic components capable of carrying out processing functions, such as a digital signal processor, a field-programmable gate array (FPGA), or a graphic board. According to other embodiments, the processor 258 may include multiple electronic components capable of carrying out processing functions. For example, the processor 258 may include two or more electronic components selected from a list of electronic components including: a central processor, a digital signal processor, a field-programmable gate array, and a graphic board. In still further embodiments the processor 258 may be configured as a graphical processing unit (GPU) including parallel computing architecture and parallel processing capabilities. Non-transitory memory 260 may store an artificial intelligence (AI) based image processing/neural network model 262, position and/or image data 264, accessory monitoring module 266, user input monitoring module 268, environment monitoring module 270, workflow monitoring module 272, and patient monitoring module 274.

In one example, the AI/neural network model 262 may include a deep learning model, comprising a plurality of parameters (including weights, biases, activation functions), and instructions for implementing the one or more deep neural networks to receive position and/or image data from the sensor system 252, and identify one or more of objects corresponding to one or more of the x-ray system components and accessories, and further identify one or more environmental parameters, and further still, identify one or more processes and actions related to one or more of mammography and biopsy. For example, AI/neural network model 262 may store instructions for implementing a deep learning module comprising one or more neural networks, such as a convolutional neural network (CNN). AI/neural network model 262 may include trained and/or untrained neural networks and may further include various data, or metadata pertaining to the one or more neural networks stored therein.

Furthermore, using input from the sensor system 252, the AI/neural network model 262 may identify a breast position, breast anatomical landmarks, patient position, patient morphology, user position, and user morphology and system and/or accessory configuration. Further, using input from the sensor system 252, the AI/neural network model 262 may evaluate breast position as well as patient position and determine one or more errors based on the evaluation. The one or more errors may include a breast positioning error, a patient positioning error, and a user error, and control the mammography system based on the error (e.g., inhibit image acquisition in response to detecting one or more error) and provide real-time based on the errors detected (e.g., as the breast is positioned, the vision sensor may obtain one or more images, which may be utilized to analyze the breast position and morphology, and provide real-time feedback based on the analysis).

In one example, a first AI/neural network model or portion of the AI/neural network model 262 may include parameters for desired patient position, including a whole body patient position, and a patient position with respect to the x-ray system, where the desired patient position is based on the imaging mode of the x-ray system and a desired view to be acquired by the imaging system. Further, a second AI/neural network model or portion of the AI/neural network model 262 may include parameters for desired breast position, including one or more compressed breast features included in the imaging volume of the x-ray system, where the desired breast position is based on the imaging mode of the x-ray system and a desired view to be acquired by the imaging system. Prior to initiating x-ray image acquisition, the sensor system 252, may be utilized to evaluate current patient position (with respect to the first module) and current breast position (with respect to the second module), and real-time feedback may be provided to the user, via the user interface, based on the evaluation. When the current patient position is in agreement with the first module and the current breast position is in agreement with the second module, x-ray image acquisition may be initiated.

Non transitory memory 260 may further store sensor/camera image data 264. Sensor/camera image data 264 may include position data/images captured by the sensor system 252. For example, position data/images captured by the sensor system 252 may include position data/images of the one or more mammography system, including x-ray system 210 including its components and accessories, the environment 226, and processes and/or actions associated with the x-ray system 210 and the environment 226. Sensor/camera image data 264 may further include patient monitoring images, user monitoring images, compressed breast images, system and/or accessory images.

Non-transitory memory 260 may further store the accessory monitoring module 266 including instructions for monitoring and analyzing the presence and current positions of the one or more accessories 214 and biopsy device 212.

Non-transitory memory 260 may further store the user input monitoring module 268 including instructions for monitoring and analyzing user input via a user interface.

Non-transitory memory 260 may further store the environment monitoring module 270 including instructions for monitoring and analyzing the environment 226, and may store workflow monitoring module 272 including instructions for monitoring and analyzing one or more processes and actions 238. Further still, non-transitory memory 260 may store patient monitoring module 274 for monitoring and analyzing one or more of patient presence, patient position, and patient movement into and out of the examination room.

Non-transitory memory 260 may further store medical image data 275. The medical image data 275 may include scan images of the body part captured by the x-ray system 210.

Upon sensing and analyzing one or more of the x-ray system 210, the environment 226, and process and action 238, the image processing system 256 may output instructions to one or more x-ray system actuators 276 based on the sensing and the analyzing. The x-ray system actuators 276 may include image acquisition actuator 278 for controlling a radiation source output from a radiation source such as radiation source 16 at FIG. 1, gantry motion actuators 280 for controlling gantry position of the x-ray system 210, and a bed position actuator, for example, based on presence or absence of an object in the environment 226. The gantry motion actuator(s) 280 may include one or more actuators for adjusting one or more of a gantry lift, a gantry rotation, and a gantry angulation, where the gantry lift motion includes movement of the gantry in an upward or downward direction along the vertical axis of the x-ray system 210, the gantry rotation is the rotation of the detector and the x-ray generation tube around a rotation axis, and the gantry angulation is the rotation of the x-ray tube while the detector remains still within an angular range of rotation.

The x-ray system actuators 276 may further include a biopsy device actuator for adjusting operation of the biopsy device, such as firing of the biopsy needle, for example, based on sensing one or more inconsistencies between the user input and the actual x-ray system configuration as further detailed below. The x-ray system actuators 276 may further include a compression paddle actuator 285 for adjusting movement of the compression paddle 222, among others.

Further, upon sensing and analyzing one or more of the x-ray system 210, breast position, patient position, the environment 226, and process and action 238, the image processing system 256 may output one or more alerts, including real-time feedback, via a user interface 286. The user interface 286 may be an example of user interface 56 at FIG. 1. Further, the processing system 256 may be configured to update image acquisition input 292 on the user interface 286 and adjust one or more of x-ray system set-up, configuration, and operation accordingly. Further still, the processing system may be configured to update accessory information input 294 on the user interface 286 and adjust x-ray system set-up, configuration, and operation accordingly.

Figure 3:
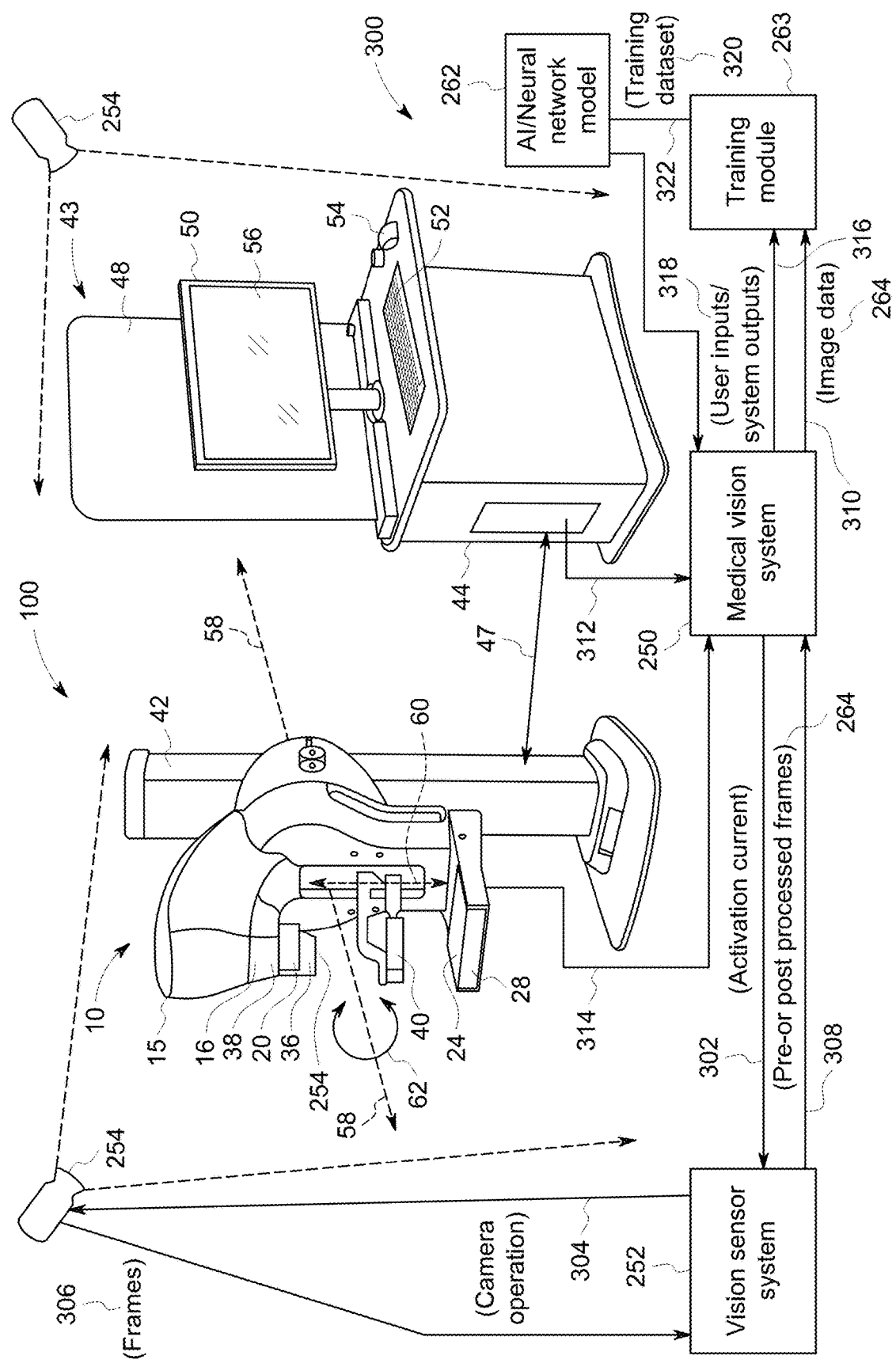
FIG. 3 is a schematic illustration of a method for on-site training an artificial intelligence model for evaluating one or more of a breast position, patient position, patient and/or breast morphology, user position, and user morphology, according to an embodiment of the disclosure.
Figure 4:
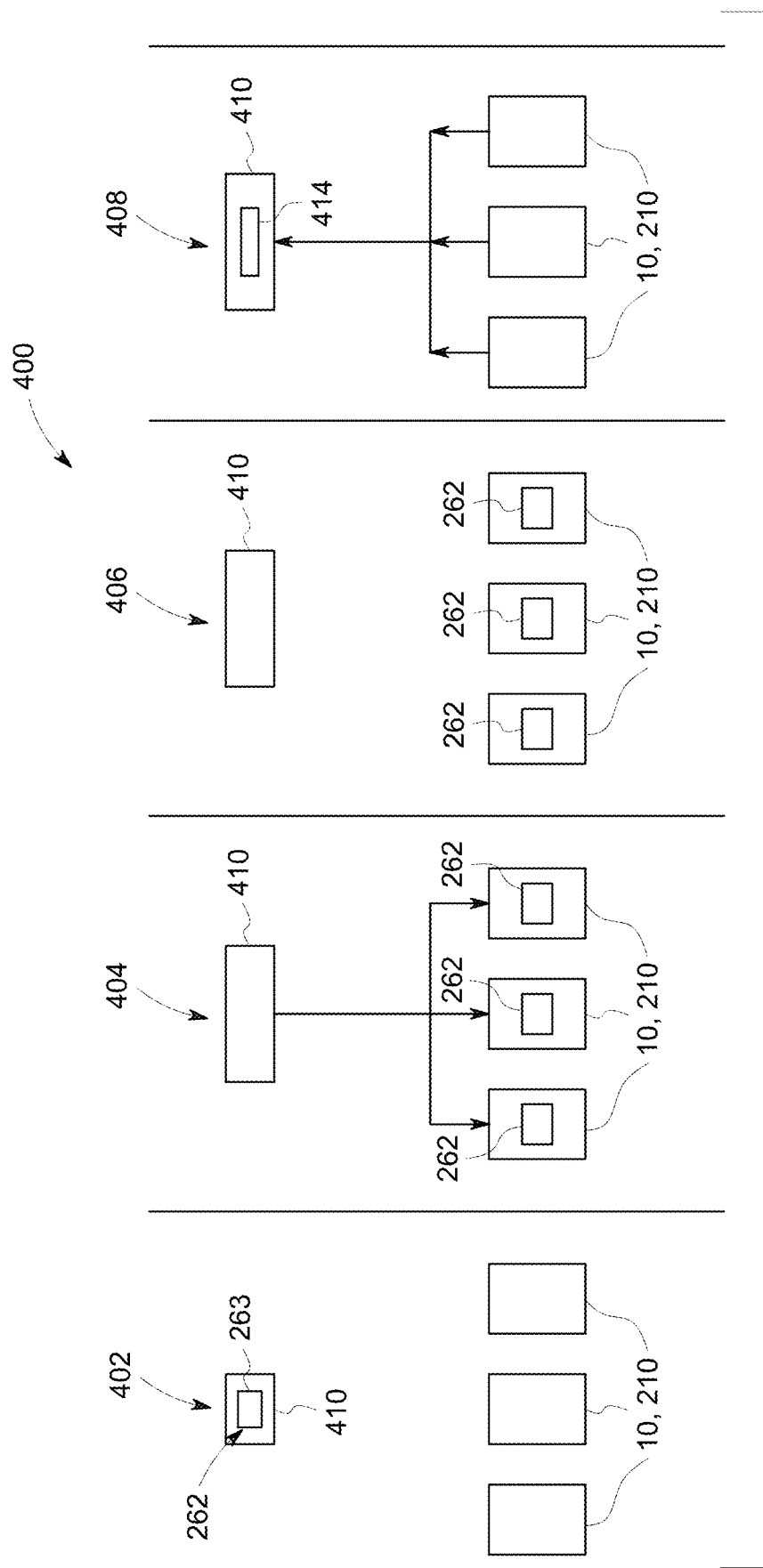
FIG. 4 is a flowchart of a method for on-site training an artificial intelligence model for evaluating one or more of a breast position, patient position, patient and/or breast morphology, user position, and user morphology, according to another embodiment of the disclosure.

Referring now to FIGS. 2 and 3, non-transitory memory 260 may further store an AI/neural network training module 263 and/or instructions for the implementation and operation of the training module 263, which comprises instructions for training one or more of the AIs and/or deep neural networks stored in AI/neural network model 262. Alternatively, the training module 263 and stored instructions for operating the training module 263 can be stored in a non-transitory memory (not shown) that is disposed remote from, but operably connected to the imaging system 200.

The training for the AI/neural network model 262 may be performed with training data supplied to the training module 263 by the image processing system 265/processor 258 for one or more imaging procedures that are performed using the imaging system 200. In particular, the training data includes the various inputs to and/or outputs from the imaging system 200 for a particular imaging procedure performed by the imaging system 200.

In order to provide the training module 263 with the truths to be employed in the training of the AI/neural network model 262, the image processing system 256/processor 258 can provide the training module 263 with the known parameters for an individual imaging procedure performed by the imaging system 200. For example, the training data set supplied to the training module 263 can include the user inputs regarding various parameters for the particular imaging procedure, such as the laterality, view, patient position, and other imaging system configuration selections for the imaging procedure.

The training dataset supplied to the training module 263 further can include the internal system outputs from various system algorithms (not shown) that are employed by the image processing system 256 to provide information to the image processing system 256, such as the output from the second AI/neural network model or portion of the AI/neural network model 262 concerning the detected current breast position, such as, for example, an internal system output from an AI/image processing algorithm performed on the X-ray images to determine if the breast is correctly positioned. This internal system output is obtained from a process already being performed by the system 100 and function as one of the one or more truths supplied to the training module 263. These user inputs and/or internal system algorithm outputs are employed by the training module 263 alone or in combination with one another as the truths or evaluation parameters for the AI/neural network model 262.

Further, the training data sent to the training module 263 by the image processing system 256/processor 258 includes the sensor/camera image data 264, which can include the position data and/or camera images of the compressed breast, camera images of a phantom, each of which correspond to the imaging procedure associated with the truths, i.e., the user inputs and/or system algorithm outputs.

It should be understood that image processing system 256 shown in FIG. 2 is for illustration, not for limitation. Another appropriate image processing system may include more, fewer, or different components.

Turning to FIG. 3, a high-level flow chart illustrating a method 300 employed by the training module 263 for obtaining a training dataset from an imaging procedure and training the AI/neural network model 262 using the training dataset is shown. In particular, the method 300 can be implemented during operation of an imaging system, such as the x-ray system 100 or 200 of FIG. 1 or 2, prior to initiating image acquisition in order to train the AI/neural network model 262 with regard to the evaluation of one or both of a position of a body part to be imaged with respect to the x-ray imaging system, and a position of the patient with respect to the x-ray system.

To train the AI/neural network model 262 according to method 300, initially the image processing/medical vision system 250 senses or determines an activation event in step 302, such as the vision system 250 determining a final (locked) position of the compression paddle 222 after positioning the patient breast between the paddle 222 and the detector, and moving the paddle 222, such as through the use of the paddle actuator 285, to place the paddle 222 at the desired location for compression of the breast, for example. Other types of activation events that can be sensed by the image processing/medical vision system 250 relate to various operating conditions and/or configurations of the x-ray system 10,210 that illustrate that the x-ray system 10,210 is in position for the evaluation and/or determination of the position and/or orientation of one or more parts of the x-ray system 10,210 and/or patient breast prior to the initiation of the imaging procedure. In response to the activation event 302, the medical vision system 250 operates the sensor system 252 including sensors/cameras 254 in step 304 to obtain position data and/or patient monitoring images and/or compressed breast images, among others, that are received by the sensor system 252. These position data/images or frames 306 are then transmitted in step 308 by the sensor system 252 to the medical vision system 250 for storage as the sensor/camera image data 264. The frames 306/sensor/camera image data 264 can be either pre- or post-processed, and are forwarded by the image processing system 256/processor 258 to the training module 263 in step 310.

In addition to the frames/sensor/image data 306, the medical vision system 250 receives user inputs 312 from user interface 286 and/or algorithm outputs 314 the x-ray imaging system 10,210 corresponding to the selected imaging parameters and system configuration for the imaging procedure to be performed. The medical vision system 250 provides these system inputs and outputs to the training module 263 in step 316 to be employed as the truth inputs 318 for the training module 263. The frames/sensor/image data 264 and truth inputs 318 from the imaging procedure being run on the imaging system 10,210 for a training dataset 320 that is subsequently transmitted by the training module 263 to the AI/neural network model 262 in step 322. The AI/neural network model 262 performs an evaluation on the training dataset 320 to determine various attributes of the frames/sensor/image data 264 and to both train the AI/neural network model 262 and to test/validate the determination(s) of the AI/neural network model 262 as to whether the frames/sensor/image data 264 corresponds with the parameters identified by the truth inputs 318 for the imaging procedure during which the frames/sensor/image data 264 was obtained. In this manner, the AI/neural network model 262 is trained using data obtained directly from the x-ray imaging system 10,210 incorporating the AI/neural network model 262 and training module 263, thereby omitting any problems or concerns with regard to the collection of the training dataset, as with prior training dataset collection practices.

With regard to the manner of operation of the training of the AI/neural network model 262 using the method 300, a number of options are available. Initially, the method 300 can be performed in a continuous learning process using data obtained on a number of imaging procedure performed utilizing the x-ray imaging system 10,210. In the continuous learning process, once the outputs from the AI/neural network model 262 of the method 300 based on the imaging procedures reach a certain specified level of accuracy, such as verified by a validation dataset (not shown) applied to the AI/neural network model 262, the configuration of the AI/neural network model 262 can be switched from continuous learning to an automatic mode, where the training module 263 is disabled, and the frames/sensor/image data 264 are supplied directly to the AI/neural network model 262 for feature detection and/or evaluation of laterality, view, breast position monitoring, sample presence and so on.

In a second alternative for the operation of the method 300, the method 300 can be operated in an active learning mode. In active learning mode, which can be employed after a continuous learning process has been utilized on the AI/neural network model 263, after the AI/neural network model 262 outputs an inference confidence score with regard to each training dataset 320 for a particular imaging procedure that is provided to the AI/neural network model 262 by the training module 263. If the inference confidence score is above a certain preset threshold determined by a user or by the training module 263, the AI/neural network model 262 can be maintained in an automatic feature detection operational configuration, as described previously. However, if the inference confidence score from the AI/neural network model 262 is below the threshold value the AI/neural network model 262 is switched back to training mode and the training module 263 provides the AI/neural network model 262 with additional training datasets 320 from further imaging procedures performed by the x-ray imaging system 10,210 until the outputs of the AI/neural network model 262 are validated and/or exceed the threshold values. In addition, if the user input is altered, i.e., if the user changes the model answer, the AI/neural network model 262 is switched back to training mode and the training module 263 provides the AI/neural network model 262 with additional training datasets 320 corresponding to imaging procedures with the newly specified user inputs.

The prior modes of operation of the training method 300 rely on training datasets formed using user inputs/system outputs and image data obtained from imaging procedures performed by a single x-ray imaging system 10,210 on which the AI/neural network model 262 and training module 263 are stored, thereby maintaining the patient data on site. In a third option, the method 300 is operated in a federated learning or personalized federated learning model. In this embodiment, as illustrated schematically in FIG. 4, initially in step 402 of the method 400, the AI/neural network model 262 is formed outside of the x-ray imaging systems 10,210 that it is to be trained on, e.g., on a central server 410, which can be remote from the imaging systems 10,210, which can also be remote from one another. In step 404 the untrained model 262 is transmitted to or otherwise installed on the individual x-ray imaging systems 10,210 in conjunction with the training module 263 from the central server 410. The AI/neural network model 262 is subsequently trained in step 406 on the individual x-ray imaging systems 10,210 in one of the aforementioned manners of method 300, until the model 262 is validated and/or reaches a predetermined accuracy threshold. Then, in step 408 the trained models 262 are retrieved from each of the individual x-ray imaging systems 10,210 by the central server 410 without any transmission or retention of any of the data from the training datasets utilized to train the models 262. The central server 410 then pools or aggregates the results of each of the trained models 262 to achieve a global trained model 414 that can be utilized on each of the individual x-ray imaging systems 10,210 to provide the feature detection functions for the individual x-ray imaging system 10,210.

In each iteration or embodiment of the training method 300,400 for training of the AI/neural network model 262 with the training module 263 disposed within the individual x-ray imaging system 10,210, the data 312,314,316,264 utilized to for the training datasets 320 is obtained in a continuous manner directly from imaging procedures performed utilizing the x-ray imaging system 10,210. In this manner the data remains secure and is not transmitted out of the clinical environment for the x-ray imaging system 10,210, preserving the privacy and confidentiality of the patient information contained within the training dataset 320. Further, in each embodiment of the method 300,400, the information forming the training dataset 320 is obtained in a seamless manner during the normal operation of the x-ray imaging system 10,210, such that the performance of the method 300,400 does not alter the operation or workflow of the x-ray imaging system 10,210 for the technician an any manner, e.g., the method 300,400 operates completely in the background of the normal operation of the x-ray imaging system 10,210 when performing x-ray imaging procedures. Further, the method 300,400 of training the AI/neural network model 262 is completely transparent to the user and does not require any modification of the manner in which the user operates the system 10,210, while also negating the need for the user to actively provide annotations to the x ray images and/or other input data for use in training the AI/neural network model 262.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for training a sensor-based feature detection artificial intelligence (AI) model for an x-ray mammography system, the method comprising the steps of:
   a. providing an x-ray mammography system including a database for storing instructions for operation of a feature detection AI model, and a sensor detection system including a sensor for generating sensor data of the x-ray mammography system or a patient;
   b. inputting parameters for an imaging procedure to be performed by the x-ray mammography system;
   c. positioning a patient breast proximate the x-ray mammography system;
   d. obtaining sensor data with the sensor detection system;
   e. providing at least one of the input parameters, one or more internal system outputs from control algorithms stored in the database, and combinations thereof, with the sensor data to a training module to form a training dataset; and
   f. providing the training dataset to the feature detection AI model.

2. The method of claim 1, further comprising the step of performing the imaging procedure concurrently with providing the training dataset to the feature detection AI model.

3. The method of claim 1, wherein the sensor is a camera that is operable to obtain camera images of the position of the x-ray mammography system and the patient as the sensor data.

4. The method of claim 1, further comprising the steps of:
   a. receiving one or more internal system outputs from control algorithms stored in the database in response to the input parameters for the imaging procedure; and
   b. providing the system outputs with the input parameters and the sensor data to the training module to form the training dataset.

5. The method of claim 4 wherein the step providing the input parameters, the internal system outputs and the sensor data to the training module comprises utilizing the input parameters and the system outputs as truths for the training dataset.

6. The method of claim 1, wherein the method is performed continuously, with the training dataset provided to the feature detection AI model with each imaging procedure performed with the x-ray mammography system.

7. The method of claim 1, wherein the method is performed automatically, with the training dataset provided to the feature detection AI model with each imaging procedure performed with the x-ray mammography system.

8. The method of claim 1, wherein the method is a federated method, with the training dataset provided to the feature detection AI model with each imaging procedure performed with each x-ray mammography system.

9. The method of claim 1, wherein the training dataset is retained within the x-ray mammography system.

10. The method of claim 1, wherein the training dataset is not transmitted externally of the x-ray mammography system.

11. The method of claim 1, wherein the step of obtaining sensor data comprises obtaining a number of images of the x-ray mammography system.

12. The method of claim 1, wherein the step of obtaining sensor data comprises obtaining a number of images of at least one of the patient, the patient breast and combinations thereof.

13. The method of claim 1, wherein the step of obtaining sensor data comprises obtaining a number of images of a position and a configuration of the x-ray mammography system and at least one of a position and a morphology of at least one of the patient, the patient breast and combinations thereof.

14. The method of claim 1, wherein the step of obtaining the sensor data from the sensor detection system comprises:
   a. sensing an activation event; and
   b. operating the sensor detection system to obtain the sensor data.

15. The method of claim 14 wherein the step of positioning the patient breast proximate the x-ray mammography system comprises:
   a. placing the patient breast between a compression paddle and a detector of the x-ray mammography system;
   b. moving the compression paddle into a desired position to compress the patient breast between the compression paddle and the detector; and
   c. locking the compression paddle in the desired position, wherein the sensed activation event is the locking of the compression paddle.

16. The method of claim 1, wherein the step of providing the sensor data to the training module comprises providing pre-processed sensor data, post-processed sensor data, and combinations thereof to the training module.

17. An x-ray mammography system, comprising:
 a. a gantry disposed on a support surface and including an x-ray source, and an x-ray detector alignable with the x-ray source;
 b. an image processing system operably connected to the gantry to control operation of the x-ray source and x-ray detector to generate x-ray image data in an imaging mode for the mammography system, the image processing system including a processor for processing the x-ray image data from the detector, a database operably connected to the processor and storing instructions for operation of a feature detection AI model and a training module therein; and
 c. a sensor detection system disposed on the gantry and operably connected to the image processing system, the sensor detection system including at least one sensor operable to generate sensor data of the gantry or a patient,
 wherein the training module is configured to receive at least one of user input parameters for an imaging procedure to be performed by the x-ray mammography system, one or more internal system outputs from control algorithms stored in the database, and combinations thereof, and sensor data from the sensor detection system to form a training dataset for use in training the feature detection AI model.

18. The x-ray mammography system of claim 17, wherein the training module is configured to be operated concurrently with an imaging procedure performed using the x-ray mammography system.

19. The x-ray mammography system of claim 17, wherein the training module is configured to be operated in a continuous learning mode.

20. The x-ray mammography system of claim 17, wherein the training module is configured to be operated in a federated learning mode.

* * * * *